United States Patent [19]

Gengnagel et al.

[11] 3,970,667
[45] July 20, 1976

[54] PROCESS FOR THE PREPARATION OF PURE TOLUTRIAZOLES

[75] Inventors: Kurt Gengnagel, Offenbach, Main; Theodor Papenfuhs, Frankfurt am Main, both of Germany

[73] Assignee: Hoechst Aktiengesellschaft, Frankfurt am Main, Germany

[22] Filed: Oct. 8, 1974

[21] Appl. No.: 513,125

[30] Foreign Application Priority Data
Oct. 13, 1973  Germany............................ 2351595

[52] U.S. Cl............................................ 260/308 B
[51] Int. Cl.². ................................ C07D 249/16
[58] Field of Search ................................ 260/308 B

[56] References Cited
UNITED STATES PATENTS

| | | | |
|---|---|---|---|
| 2,861,078 | 11/1958 | Miller et al. | 260/308 B |
| 3,564,001 | 2/1971 | Long | 260/308 B |
| 3,639,431 | 2/1972 | Meteer et al. | 260/308 B |
| 3,732,239 | 5/1973 | Spatz et al. | 260/308 B |

*Primary Examiner*—Paul M. Coughlan, Jr.
*Attorney, Agent, or Firm*—Connolly and Hutz

[57] ABSTRACT

The process for the preparation of tolutriazoles by diazotation of toluylene-o-diamines and subsequent ring closure to form the tolutriazole ring, was improved and the tolutriazoles are now obtained in a simpler way and in a pure form. The improvement comprises dissolution of the tolutriazoles without preceding isolation after their synthesis by means of an alkaline agent, preferably a sodium hydroxide solution of 20 – 33% strength, and subsequent precipitation at a pH of from 4.5 to 6 by addition of a mineral acid, preferably nitric acid or hydrochloric acid, and avoids a subsequent technically complicated and expensive purification process as well as the use of organic solvents. The tolutriazoles obtained according to this novel process are sufficiently pure for the use as corrosion inhibition.

4 Claims, No Drawings

PROCESS FOR THE PREPARATION OF PURE TOLUTRIAZOLES

The present invention relates to an improved process for preparing pure tolutriazoles and the mixtures thereof.

Tolutriazoles (4- or 5-methyl-1H-benzotriazole) and the mixtures thereof are used to a large extent on an industrial scale as corrosion inhibitors for metal surfaces and functional liquids.

They are prepared on an industrial scale by diazotation of toluylene-o-diamines or the mixtures thereof with alkali nitrite and an acid, expediently with sodium nitrite and acetic acid, and subsequent ring closure to form the tolutriazole. Depending on the quality of the toluylene-o-diamines, the products thus obtained have very different degrees of purity, so that they must be subsequently purified before being used.

Thus, it is already known how to extract the acid solution containing acetic acid, with chloroform after the reaction, to wash to chloroform solution, to distill off the solvent and to recrystallize the crude tolutriazole from benzene (cf. U.S. Patent Specification No. 3,732,239).

However, such a process is very complicated as concerns the technical equipment, since it includes a recovering and purification of the solvents.

It has now been found that tolutriazoles and the mixtures thereof may be obtained in a simpler way in a pure form by diazotation of toluylene-o-diamines with the aid of alkali nitrite and an organic acid and subsequent ring closure to give tolutriazole, if the tolutriazole is dissolved by means of an alkaline agent or solution without preceding isolation and is subsequently precipitated by addition of a mineral acid at a pH-value of about 4.5 to 6, preferably 5 to 5.5.

The process is carried out in the following manner: a toluylene-o-diamine, for example a mixture of 2,3- and 3,4-diaminotoluene obtained on an industrial scale, is diazotized by addition of sodium nitrite and acetic acid at about 0° to 5°C, whereby, when removing cooling, the triazole ring closure occurs with an increasing temperature. Subsequently, the mixture is diluted with water, made alkaline with alkali, advantageously with a sodium hydroxide solution, and after one or more filtrations with charcoal, kieselguhr and sodium dithionite it is adjusted to a pH-value of about 4.5 to 6.5, expediently to about 5 to 5.5, by addition of a mineral acid, preferably nitric acid of about 40–75% or hydrochloric acid of about 20–25% strength. The tolutriazole precipitated is suction-filtered, washed with water and dried.

The tolutriazole obtained by this way is sufficiently pure for being used as corrosion inhibitor.

The process may be applied continuously and discontinuously. As compared with the known process the process of the invention represents a considerable technical progress, since it avoids the use of organic solvents and leads to a very pure product by operations which may be easily carried out on an industrial scale.

The following Example illustrates the invention. Parts and percentages are by weight unless stated otherwise.

EXAMPLE 200 parts of toluylene-o-diamine were introduced into a mixture of 500 parts by volume of water of about 45°C and 210 parts of a technical grade acetic acid. The mixture was stirred for 30 minutes at 40°–45°C until the base was dissolved completely. Then it was mixed with 2 parts of a defoaming agent, the solution was cooled to 3°–4°C and within 3 to 4 minutes after removing the cooling bath, 300 parts of a 40% sodium nitrite solution were introduced under the surface, whereby, with a rapid increase of the temperature to 75°C, the triazol ring closure occured.

Stirring was continued for 30 minutes and the mixture was mixed with 500 parts by volume of water. At about 45°C, 500 parts of a 33% sodium hydroxide solution were added dropwise within 10 minutes, so that the temperature was maintained at about 50°C. In an interval of 10 minutes each 10 parts of charcoal were added five times, and 10 parts of kieselguhr were added to the last amount of coal. After the addition of 10 parts of sodium dithionite stirring was continued for 10 minutes, then the mixture was clarified. The filtered residue was washed with 200 parts by volume of water. 10 parts of charcoal and after 10 minutes another 10 parts of charcoal, 10 parts of kieselguhr and 10 parts of sodium dithionite were added once more to the filtrate. After 10 minutes the whole was clarified again and the filter residue was washed with 100 parts by volume of water.

The filtrate was cooled to 10°C. With further cooling with ice water, the pH-value was regularly adjusted to 5–5.5 within 2 hours at a temperature of about 8°–10°C by slowly adding dropwise about 330 parts of a 62% nitric acid. Then the mixture was cooled to 3°–4°C and stirring was continued for one hour at this temperature and at a pH-value of 5 to 5.5. The tolutriazole precipitated was suction-filtered and washed with about 1000 parts by volume of ice water on the whole, in several portions and dried at 40°C. 184 Parts = 84.4% of the theory of tolutriazole were obtained in form of a clear yellow powder having a pure content of 98.7% and a melting point of 80° to 82°C.

What we claim is:

1. In a process for the preparation of a tolutriazole by diazotation of a toluylene-o-diamine by means of an alkali nitrite and an organic acid, subsequent ring closure to form the tolutriazole and subsequent purification of the tolutriazole obtained, the improvement comprising carrying out the purification by diluting the reaction mixture with water, then making it alkaline with alkali, adding charcoal, kieselguhr and sodium dithionite, filtering it, adjusting it to a pH-value of about 4.5 to 6.5 by addition of a mineral acid, and separating the precipitated tolutriazole.

2. Process as claimed in claim 1 wherein nitric acid is used as mineral acid.

3. Process as claimed in claim 1, wherein the pH is 5 to 5.5.

4. Process as claimed in claim 1, wherein the alkali used to make said reaction mixture alkaline is sodium hydroxide.